(12) United States Patent
Withers

(10) Patent No.: US 10,632,283 B2
(45) Date of Patent: Apr. 28, 2020

(54) CATHETER PLACEMENT DEVICE

(71) Applicant: Teresa Kathryn Withers, Benowa (AU)

(72) Inventor: Teresa Kathryn Withers, Benowa (AU)

( * ) Notice: Subject to any disclaimer, the term of this patent is extended or adjusted under 35 U.S.C. 154(b) by 133 days.

(21) Appl. No.: 14/909,677

(22) PCT Filed: Aug. 1, 2014

(86) PCT No.: PCT/AU2014/050167
§ 371 (c)(1),
(2) Date: Feb. 2, 2016

(87) PCT Pub. No.: WO2015/013771
PCT Pub. Date: Feb. 5, 2015

(65) Prior Publication Data
US 2016/0175561 A1    Jun. 23, 2016

(30) Foreign Application Priority Data
Aug. 2, 2013  (AU) ................................ 2013902909

(51) Int. Cl.
*A61M 25/01*     (2006.01)
*A61B 17/34*     (2006.01)
(Continued)

(52) U.S. Cl.
CPC ............. *A61M 25/01* (2013.01); *A61B 90/11* (2016.02); *A61B 17/3415* (2013.01); *A61B 2017/00907* (2013.01); *A61B 2090/103* (2016.02); *A61M 2025/0177* (2013.01); *A61M 2039/025* (2013.01); *A61M 2039/0273* (2013.01); *A61M 2210/0687* (2013.01)

(58) Field of Classification Search
CPC .......... A61M 25/01; A61M 2025/0273; A61M 2025/0286; A61M 2025/028; A61M 39/0247; A61M 2039/025; A61M 27/006
See application file for complete search history.

(56) References Cited

U.S. PATENT DOCUMENTS 3,633,579 A    1/1972  Alley ......................... 128/214.4
4,516,968 A *  5/1985  Marshall ............... A61M 25/02
                                                    128/DIG. 26
(Continued)

FOREIGN PATENT DOCUMENTS

GB            922007      3/1963
WO    WO 2004/107953 A2  12/2004
(Continued)

OTHER PUBLICATIONS

"Definition of Tooth", Merriam-Webster.com, accessed Mar.19, 2019 (Year: 2019).*
(Continued)

*Primary Examiner* — Rebecca E Eisenberg
*Assistant Examiner* — Tasnim Mehjabin Ahmed
(74) *Attorney, Agent, or Firm* — Stein IP, LLC

(57) ABSTRACT

A catheter placement device including a location portion for locating the device relative to a body part and a tubular up stand extending upwardly from the location portion and having a bore therethrough, the bore being oriented such that the bore extends angularly relative to the body part in use.

16 Claims, 7 Drawing Sheets

(51) Int. Cl.
*A61B 90/11* (2016.01)
*A61B 17/00* (2006.01)
*A61B 90/10* (2016.01)
*A61M 39/02* (2006.01)

(56) References Cited

U.S. PATENT DOCUMENTS

| | | | | |
|---|---|---|---|---|
| 4,821,716 | A * | 4/1989 | Ghajar | A61B 17/1695 604/174 |
| 4,903,707 | A | 2/1990 | Knute et al. | 128/748 |
| 5,234,455 | A * | 8/1993 | Mulhollan | A61B 17/3421 604/164.11 |
| 5,653,718 | A * | 8/1997 | Yoon | A61B 17/34 604/174 |
| 6,206,885 | B1 | 3/2001 | Ghahremani et al. | 606/96 |
| 7,985,205 | B2 * | 7/2011 | Adams | A61J 15/0015 604/174 |
| 8,932,263 | B2 * | 1/2015 | Rosenberg | A61M 25/02 604/174 |
| 2004/0243145 | A1 * | 12/2004 | Bobo, Sr. | A61B 5/031 606/129 |
| 2005/0203486 | A1 * | 9/2005 | Sommerich | A61M 39/0247 604/891.1 |
| 2007/0078430 | A1 * | 4/2007 | Adams | A61M 25/09041 604/500 |
| 2012/0302959 | A1 * | 11/2012 | Fielder | A61B 17/1739 604/151 |
| 2012/0323217 | A1 * | 12/2012 | Abrahams | A61B 17/3421 604/506 |
| 2015/0297873 | A1 * | 10/2015 | Jenkins | A61M 25/02 604/540 |

FOREIGN PATENT DOCUMENTS

| | | |
|---|---|---|
| WO | WO 2011/098769 A1 | 8/2011 |
| WO | WO 2013/015897 A1 | 1/2013 |

OTHER PUBLICATIONS

Dictionary.com, Definition of Catheter, (2019) (Year: 2019).*
Extended European search report dated Feb. 8, 2017, issued by the International Patent Office in corresponding application EP 14832425.4.
International Search Report dated Dec. 24, 2014, issued to the corresponding International Application No. PCT/AU2014/050167.

* cited by examiner

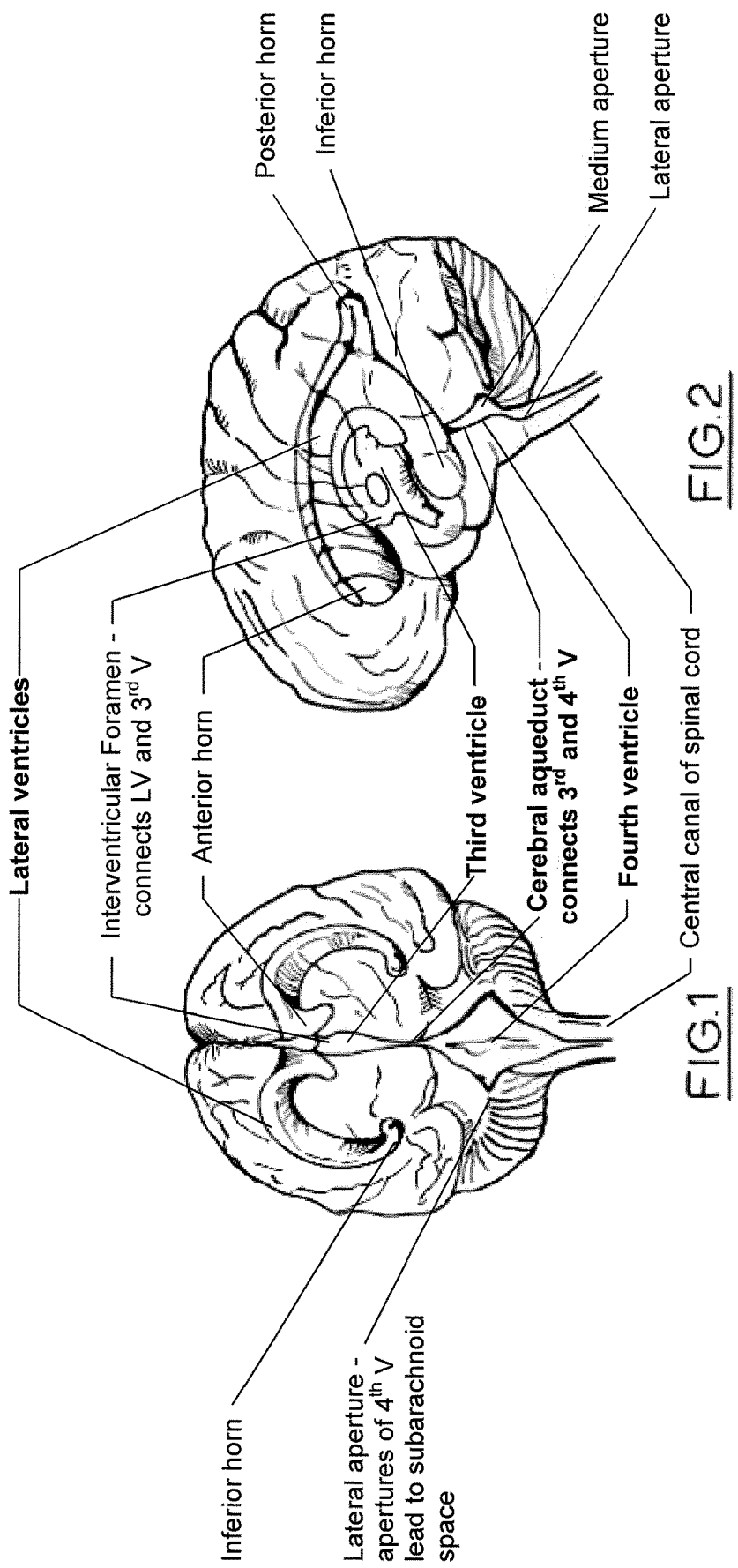

CATHETER PLACEMENT DEVICE

CROSS-REFERENCE TO RELATED APPLICATIONS

This application is a national stage of International Application No. PCT/AU2014/050167, filed Aug. 1, 2014, which claims the benefit of priority to Australian Application No. 2013902909, filed Aug. 2, 2013 in the Australian Patent Office, the disclosures of which are incorporated herein by reference.

TECHNICAL FIELD

The present invention relates to medical devices generally and in particular to a catheter placement device to guide introduction of a catheter into a patient.

BACKGROUND ART

The brain has within it, fluid filled chambers called ventricles. A schematic illustration of the ventricles in the brain is illustrated in FIGS. 1 and 2, which are an anterior and left lateral view of the brain respectively.

The fluid which surrounds and cushions the brain and spinal cord is called cerebrospinal fluid or CSF. The ventricles are interconnected and are critical in maintaining the structure of the brain and altering pressure within the brain which is known as the intra-cerebral pressure (ICP). In the event of a change in intra-cerebral pressure (generally following some type of injury to the brain which could be caused by a knock or infection for example) it may be critical to monitor this change and if necessary, draw off some of the cerebrospinal fluid located in the ventricles in order to decrease the intra-cerebral pressure.

Intra-ventricular catheters have been used for more than 20 years to monitor cerebrospinal fluid pressure by connecting them to a pressure transducer. If the pressure is high it is possible to draw off fluid to decrease the intra-cerebral pressure.

The catheters used are typically soft but have a firm, metal stylet which runs through the centre of the catheter. The stylet is typically withdrawn once the catheter is in the correct position.

The process of placement of an intra-ventricular catheter is illustrated in FIGS. 3 to 6. As illustrated in FIG. 3, an incision 10 is typically made in the skin of the patient's head 11. A burr hole 12 is drilled into the bone of the patient's skull to create an opening for the catheter as illustrated in FIG. 4. The skin of the head is spread using retractors and a catheter is inserted manually through the burr hole 12 as illustrated in FIG. 5. The medical practitioner must manually insert the catheter 13 such that the lower end of the catheter 13 sits in a ventricle 14. A pressure transducer 15 is then connected to the outer end of the catheter to monitor the intracranial pressure as illustrated in FIG. 6.

One problem with catheters and their placement occurs if the angle of entry is not perpendicular in all planes, then there is the possibility of both a horizontal and vertical error from the desired destination point. This is illustrated schematically in FIG. 7 showing the insertion of a catheter at an angle through a patient's skull 16. Vector mathematics illustrate that a significant error rate exists in the correct placement of catheters manually.

The average length of insertion of intra-ventricular catheters placed into the intra-cerebral ventricles generally ranges from 5 to 8 cm (but is of course limited by the distance of the ventricle from the skull and the size of the ventricle). A greater angle of error at introduction, leads to a greater increase in both horizontal and vertical error as illustrated in FIG. 7. An increase in depth of penetration also exacerbates the horizontal and vertical error.

Expressed in a tabular form, Table 1 below, shows the increased horizontal and vertical error with angle of deviation from perpendicular and according to depth of penetration.

TABLE 1

Horizontal and vertical error with angle of deviation from perpendicular and depth of penetration.

| Angle of Deviation (degrees) | Depth of Penetration (cm) | Horizontal Error (cm) | Vertical Error (cm) |
|---|---|---|---|
| 10 | 5 | 0.87 | 0.07 |
| 10 | 6 | 1.04 | 0.09 |
| 10 | 7 | 1.2 | 0.1 |
| 10 | 8 | 1.39 | 0.12 |
| 20 | 5 | 1.71 | 0.30 |
| 20 | 6 | 2.05 | 0.36 |
| 20 | 7 | 2.38 | 0.42 |
| 20 | 8 | 2.74 | 0.48 |
| 30 | 5 | 2.5 | 0.66 |
| 30 | 6 | 3 | 0.8 |
| 30 | 7 | 3.5 | 0.94 |
| 30 | 8 | 4 | 1.1 |

Misplacement of an intra-ventricular catheter may lead to a failure of the catheter to function, or may inadvertently damage delicate structures within the brain causing neurological injury.

It will be clearly understood that, if a prior art publication is referred to herein, this reference does not constitute an admission that the publication forms part of the common general knowledge in the art in Australia or in any other country.

SUMMARY OF INVENTION

The present invention is directed to a catheter placement device, which may at least partially overcome at least one of the abovementioned disadvantages or provide the consumer with a useful or commercial choice.

With the foregoing in view, the present invention in one form, resides broadly in a catheter placement device including a location portion for locating the device relative to a body part and a tubular upstand extending upwardly from the location portion and having a bore therethrough, the bore being oriented such that the bore extends angularly relative to the body part in use.

The catheter placement device, of the present invention is designed to introduce a catheter to a body part or relative to the body part.

Normally, a catheter will be introduced perpendicularly as this will reduce both horizontal error and vertical error at the same time allowing correct placement of the catheter.

The present invention will typically be used for intra-ventricular catheters but can be used for any catheter in which precise placement of the catheter is important, or where introduction of a catheter at a particular angle is required.

The device of the present invention will normally be moulded, and typically, as a unitary device. It is preferably manufactured from an appropriate material for use in medical procedures or environments and therefore, a medical grade plastic material is particularly preferred. It is also preferred that the device be at least partially translucent or transparent to assist the medical practitioner with a visual guide as to the location of the catheter within the device, during insertion. It is preferred that the material used results in a substantially rigid device.

Typically, the device will be a single use device after which it will be disposed of.

The device is preferably circular in cross-sectional shape as this shape will typically allow simplified manufacturing.

The device includes a location portion for locating the device relative to a body part. The location portion will normally be a foot portion which in use, will generally abut the body part through which the catheter is inserted. Normally, the foot portion will have a substantially planar lower surface.

The location portion can have any shape, any thickness and any lateral dimension.

As to preferred dimensions, the device will usually be approximately 25 mm in diameter and approximately 25 mm in height. It is been found that these dimensions provide the required precision for maintaining the correct angle of introduction of a catheter as well as allowing the device to be easily handled manually. A further advantage with providing a relatively small diameter device is that the footprint of the device is typically small enough to account for variations in shape of the body part once the location portion abuts the body part.

Typically, the underside of the preferred foot portion may include one or more gripping configurations. The provision of one or more gripping configurations will preferably prevent or at least minimise movement of the device relative to the body part when the device is placed and typically pressed against the body surface. It is preferred that the gripping configuration(s) are such that the device can easily be moved if lifted away from the surface of the body part.

Any configuration could be used, for example a rippled surface, a roughened surface or one or more protrusions. A preferred embodiment is the provision of at least 2, and generally more than 2 teeth or similar, extending from a lower surface of the location portion. It is preferred that the teeth are pointed or tapered in order to allow engagement with the body part surrounding the catheter entry point.

It is further preferred that the teeth are located toward an outer edge of the location foot. Normally, more than two teeth are provided and usually, between four and eight teeth are provided.

In general, an intra-ventricular catheter requires a burr hole to be drilled in the skull. Typically this burr hole is a fixed size. A tubular collar may preferably extend from a lower surface of the location portion. Where provided, the tubular collar will typically be coaxial with the bore through the up stand portion. The collar is generally annular in shape and is preferably located centrally on the location portion. The tubular collar will preferably be located at least partially within the catheter entry opening or burr hole formed in the body part in order to assist with location and seating of the device relative to the body part.

The collar will normally be circular as the burr hole is typically circular. Further, the collar is typically sized to be received at least partially within the burr hole. An outer surface of the collar may taper inwardly and downwardly. The outer surface will preferably abut the periphery of the burr hole and the location foot abuts the surrounds of the burr hole in order to locate and orient the device and particularly the upstand portion.

It is particularly preferred that the tubular collar be a low profile collar and normally, extend not more than 3 mm in height from the lower surface of the location portion.

The device also preferably includes a tubular upstand extending upwardly from the location portion and having a bore therethrough, the bore being oriented such that the bore extends angularly to the body part in use.

Normally, the upstand and the bore therethrough will be substantially perpendicular to the location portion but the tubular up stand can be provided at an angle which is other than perpendicular if required. The location and orientation of the upstand relative to the location portion is normally fixed in order to maintain the angle of the bore relative to the location portion.

Generally, the upstand is annular in cross-sectional shape. The bore may taper inwardly towards the centre of the bore from an upper or outer end of the upstand to a lower or inner end but this is typically for manufacturing purposes rather than to provide enhanced functionality.

The upstand is typically approximately 25 mm in height as this has been found to be a sufficient height to keep the catheter properly oriented and to make the device small enough to be relatively easily manually located. The internal dimension of the bore is typically dimensioned to closely receive the catheter as this will assist with maintaining the proper angle of insertion. An internal dimension of the bore which is too large will still allow error to be introduced in location of the catheter. The device may be manufactured in different models in order to receive different diameter catheters and therefore the dimensions may be adjusted accordingly.

One or more bracing structures may be used in order to maintain the angle of the upstand relative to the location portion. Generally, one or more bracing members are provided, and typically at least three bracing members are provided spaced around the upstand. The bracing members will normally be buttress or web members extending between a substantially planar location portion and a sidewall of the upstand. A further advantage of providing the bracing members is that the device is then more easily manually located by a medical practitioner during use.

The device of the present invention will preferably find use in the placement of cerebral intra-ventricular catheters but can be used in relation to the introduction of any catheter to any patient, whether human or otherwise. For example, the device can be used on animals by a veterinarian.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of the invention in any way. The Detailed Description will make reference to a number of drawings as follows:

FIG. 1 is an interior view of the human brain with the location of the ventricles illustrated.

FIG. 2 is a left lateral view of the human brain with the location of the ventricles illustrated therein.

DESCRIPTION OF EMBODIMENTS

According to a particularly preferred embodiment of the present invention, a catheter placement device is provided.

As illustrated in FIGS. 8 to 13, the catheter placement device 50 of the preferred embodiment includes a location foot 17 for locating the device relative to a body part and a tubular upstand 20 extending upwardly from the location foot 17. The upstand 20 has a bore 21 therethrough oriented such that the bore 21 extends perpendicularly relative to the body part in use.

Figure 14:
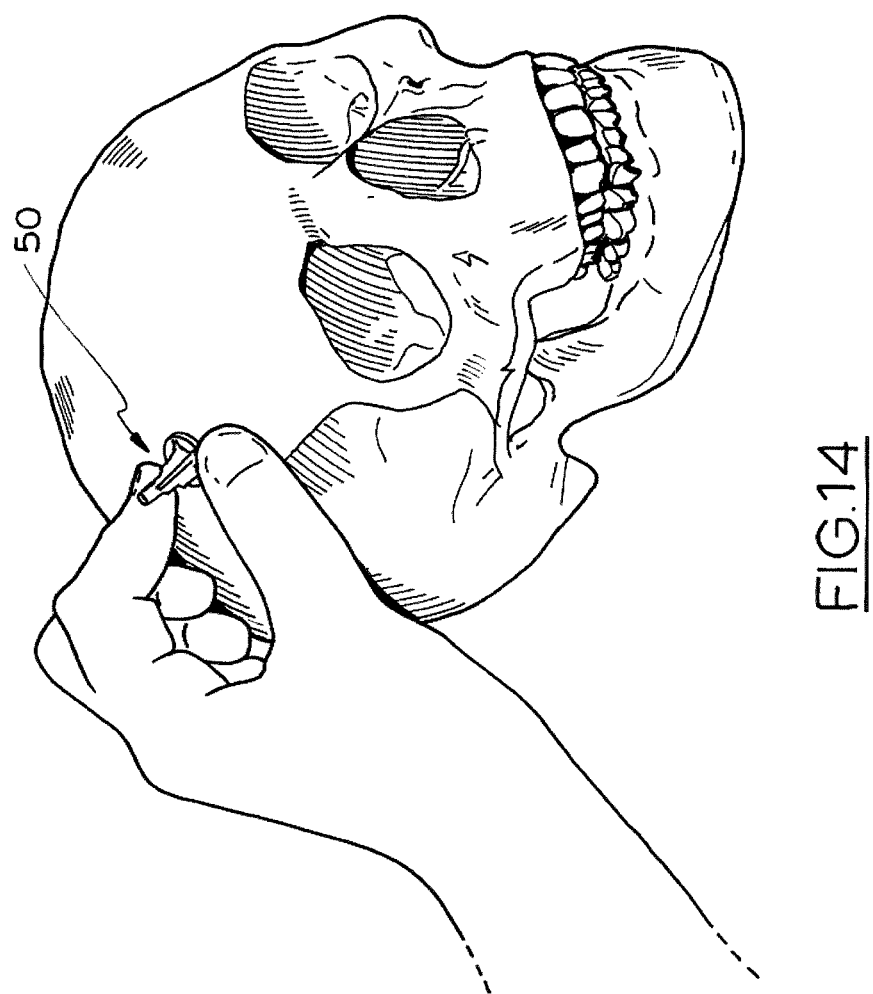

The device of the preferred embodiment is adapted to guide insertion of a cerebral intra-ventricular catheter. An intra-ventricular catheter is inserted following the process described above in relation to FIGS. 3 to 6 and the device of the preferred embodiment is used in addition to that process being manually located and maintained as illustrated in FIG. 14 during the insertion process.

The device illustrated in FIGS. 8 to 13 is moulded of an at least partially transparent medical grade plastic material. The device is a single use device after which it will be disposed of. The illustrated device is circular in cross-sectional shape as this shape will typically allow simplified manufacturing.

The location foot 17 of the illustrated embodiment abuts the skull through which the catheter 13 is inserted and has a substantially planar lower surface 10.

As to preferred dimensions, the device illustrated in FIGS. 8 to 13 is approximately 25 mm in diameter and approximately 25 mm in height. The underside of the location foot 17 includes six (6) teeth 18 extending from a lower surface of the location foot spaced about the circumference of the location foot 17. The teeth 18 are pointed or tapered in order to allow engagement with the body part surrounding the catheter entry point.

A tubular collar 22 extends from a lower surface of the location foot 17 which is coaxial with the bore 21 through the upstand 20. The collar 22 on the illustrated embodiment is annular in shape. The tubular collar is located at least partially with in the catheter entry opening or burr hole formed in the skull in order to assist with location and seating of the device relative to the skull.

The collar 22 is circular as the burr hole is typically circular. Further, the collar is typically sized to be received at least partially within the burr hole. The outer surface preferably abuts the periphery of the burr hole and the location foot 17 abuts the surrounds of the burr hole in order to locate an orient the device and particularly the upstand 20.

It is particularly preferred that the tubular collar extend not more than 3 mm in height from the lower surface of the location foot 17.

Normally, the tubular upstand 20 and the bore 21 therethrough is substantially perpendicular to the location foot 17 as illustrated. Generally, the upstand 20 is annular in cross-sectional shape. The bore 21 of the illustrated taper inwardly towards the centre of the bore 21 from an upper or outer end of the upstand to a lower or inner end but this is typically for manufacturing purposes rather than to provide enhanced functionality.

The upstand 20 is typically approximately 25 mm in height as this has been found to be sufficient height to keep the catheter properly oriented and to make the device small enough to be relatively easily manually located. The internal dimension of the bore 21 is dimensioned to closely receive the catheter as this will assist with proper insertion.

Bracing members 23 are used in order to maintain the angle of the up stand relative to the location portion. The bracing members 23 of the illustrated embodiment are buttress or web members extending between a substantially planar location foot 17 and a sidewall of the upstand 20.

Figures 4, 5:
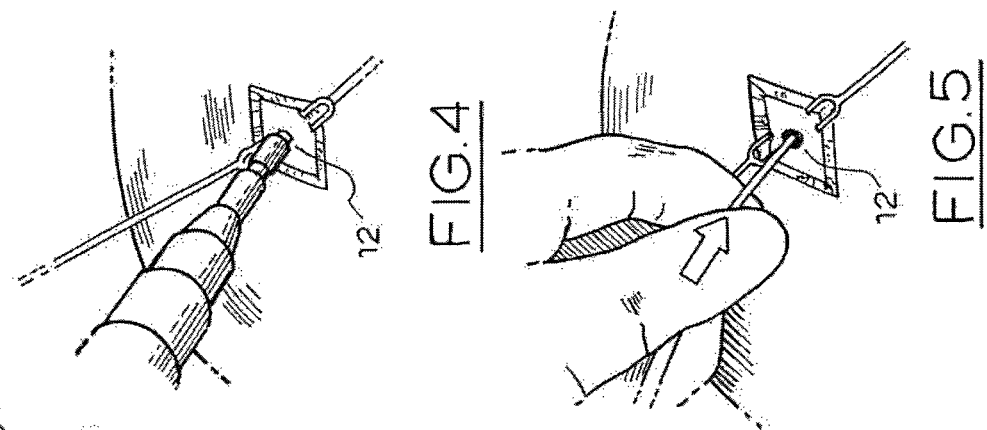
FIG. 4 is a schematic illustration of a second step of forming a hole in the skull using a burr.
FIG. 5 is a schematic illustration of a third step of manually introducing a catheter through the formed hole.
Figure 3:
FIG. 3 is a schematic illustration showing the first step of introducing an intra-ventricular catheter forming an incision in the skin of a patient's head.
Figure 7:
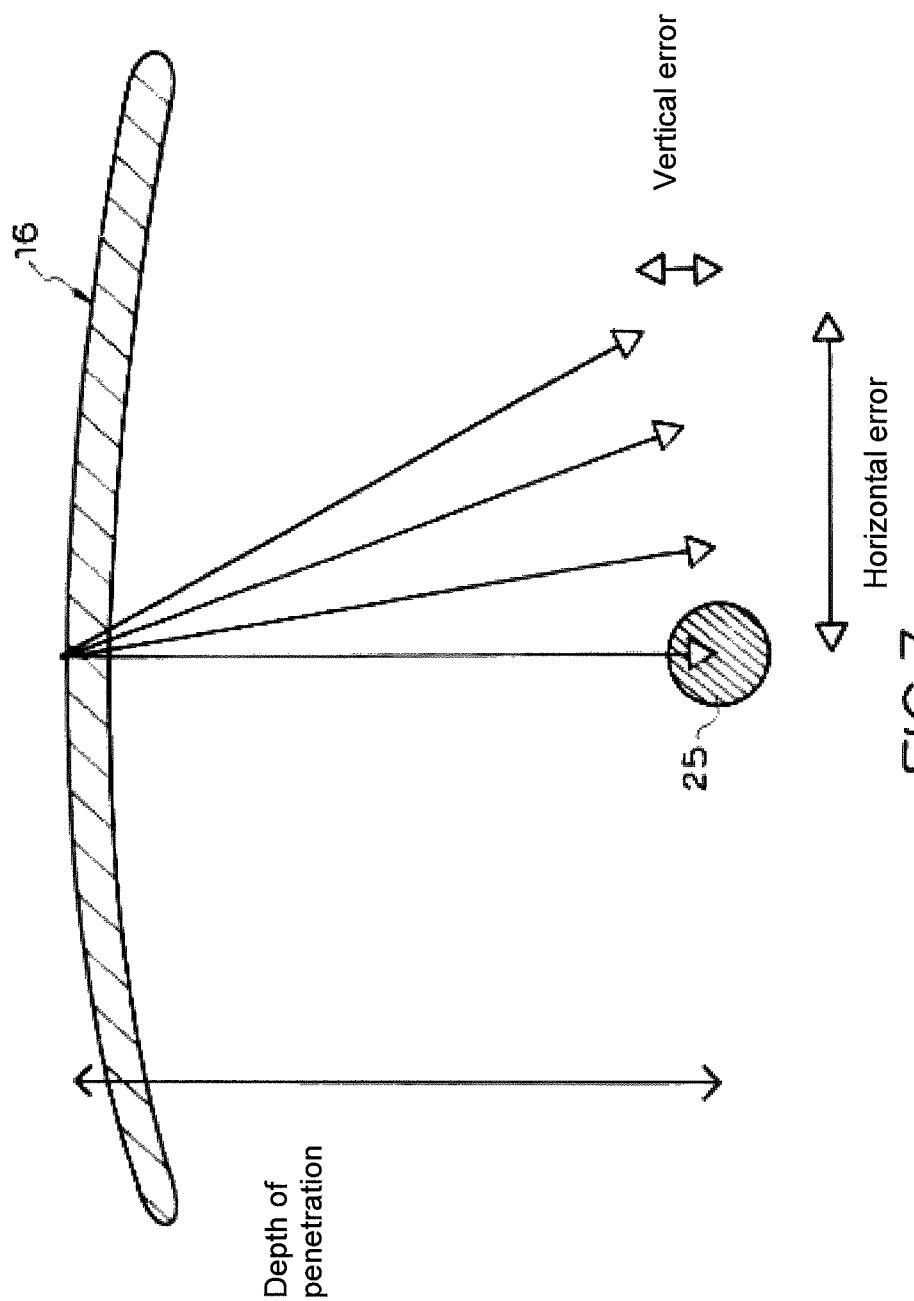
FIG. 7 is a schematic view showing the variation in final position of a catheter depending upon the angle of insertion.
Figure 9:
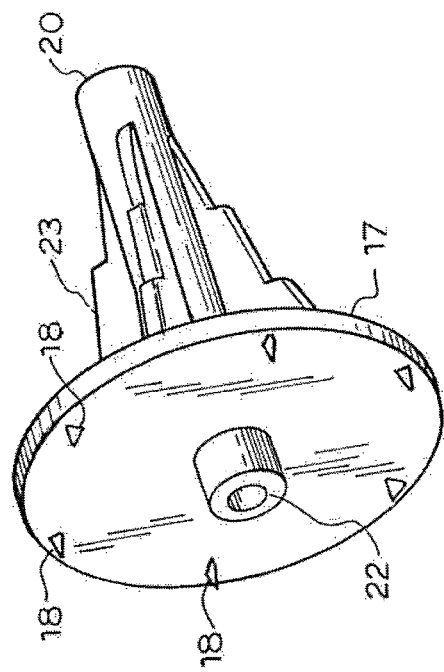
FIG. 9 is an isometric view from below of the catheter placement device illustrated in FIG. 8.
Figure 8:
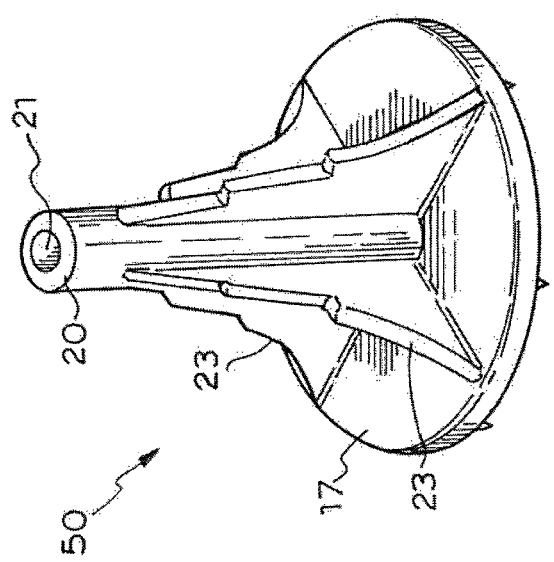
FIG. 8 is an isometric view from the front of a catheter placement device according to a preferred embodiment of the present invention.
Figure 11:
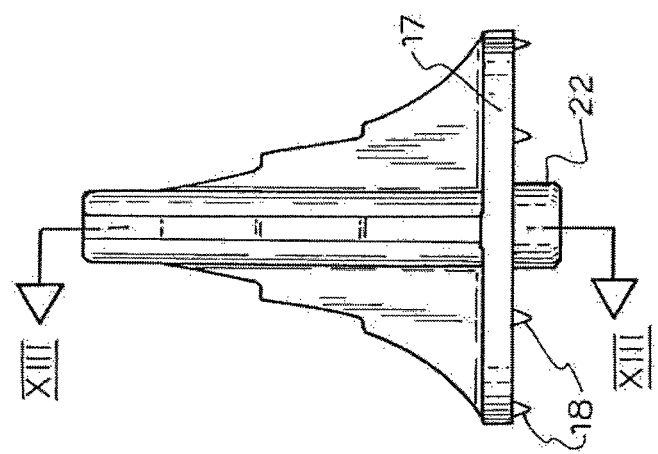
FIG. 11 is a side elevation view of the catheter placement device illustrated in FIG. 8.
Figure 10:
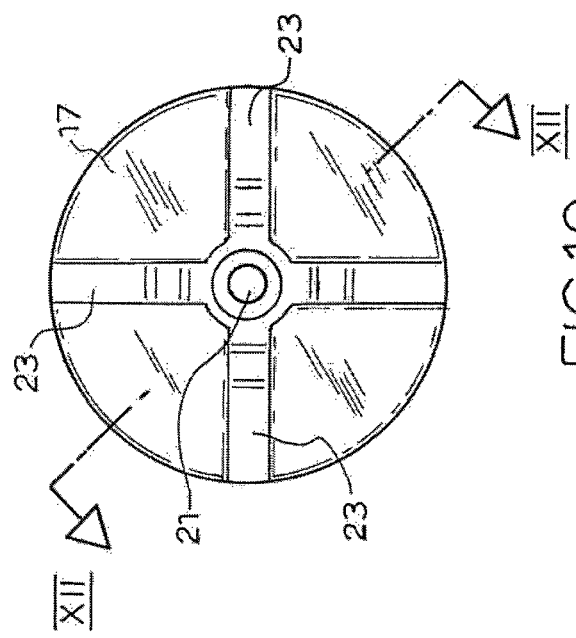
FIG. 10 is a plan view of the catheter placement device illustrated in FIG. 8.
Figure 13:
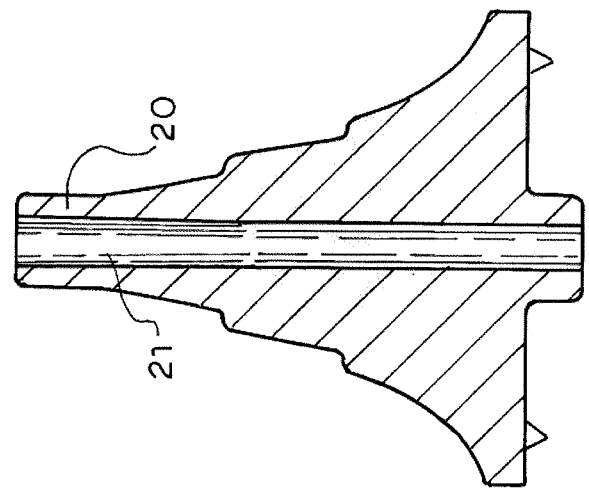
FIG. 13 is a sectional view along line XIII-XIII of the catheter placement device illustrated in FIG. 10.
Figure 12:
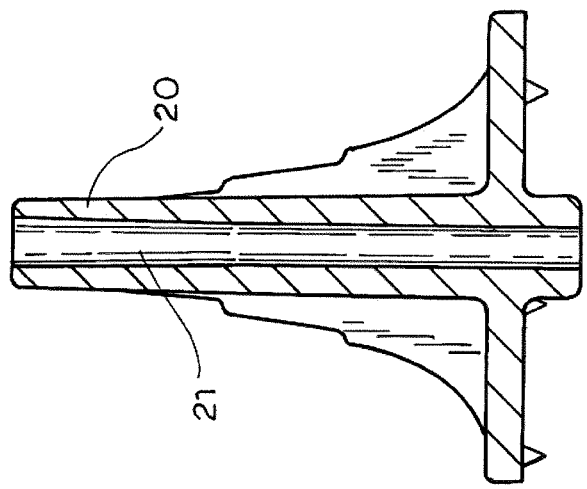
FIG. 12 is a sectional view along line XII-XII of the catheter placement device illustrated in FIG. 11.

The process of placement of an intra-ventricular catheter is generally that illustrated in FIGS. 3 to 6. As illustrated in FIG. 3, an incision 10 is made in the skin of the patient's head at the recognised landmarks for placement of an intraventricular catheter. This is known as Kochers Point. The skin of the head is then spread using retractors. A circular burr hole 12 is formed into the bone of the patient's skull to create an opening for the catheter as illustrated in FIG. 4.

At this point, the conventional process is changed. The device of the present invention is located against the skull manually with the collar partially within the burr hole and held there firmly. A catheter is inserted manually through the bore of the device which ensures that the catheter is inserted perpendicularly. The medical practitioner need then only control the depth of insertion.

Figure 6:
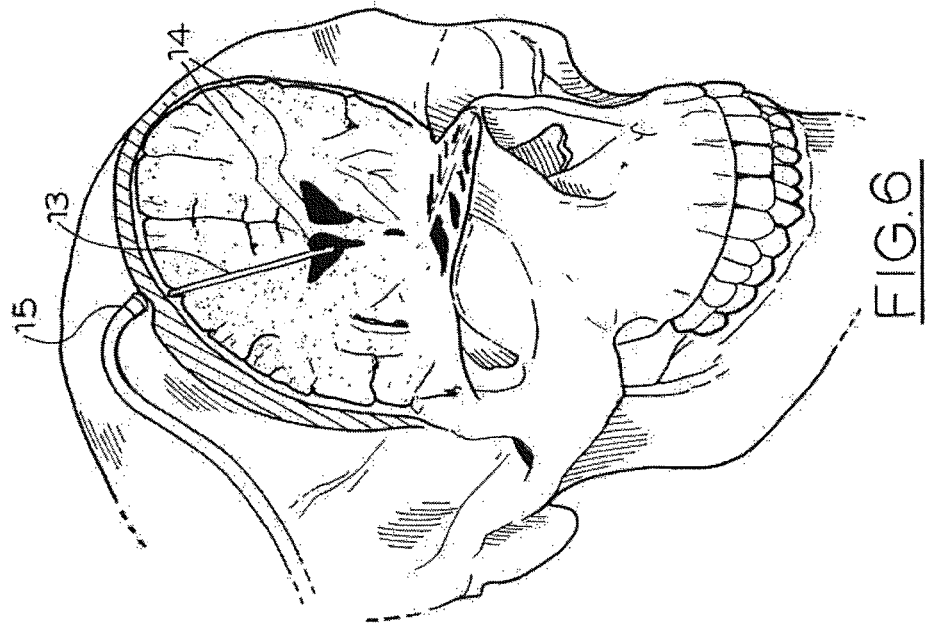
FIG. 6 is a schematic illustration of the proper placement of an intra-ventricular catheter according to the conventional method.

Once the catheter is in the correct place, the device can then be withdrawn over the catheter and disposed of. A pressure transducer 15 is then attached at the outer end of the catheter to monitor the intracranial pressure as illustrated in FIG. 6.

The manual location of the device is illustrated in FIG. 14.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearances of the phrases 'in one embodiment' or 'in an embodiment' in various places throughout this specification are not necessarily all referring to the same embodiment. Furthermore, the particular features, structures, or characteristics may be combined in any suitable manner in one or more combinations.

The invention claimed is:

1. A unitary catheter placement device formed of a single piece, the device including:
    a non-threaded, laterally extending location portion for locating the device relative to a patient's head;
    a tubular upstand extending upwardly from the location portion and having a bore therethrough, the bore being oriented such that the bore extends angularly relative to the patient's head in use,
    one or more bracing member between the location portion and the tubular upstand,
    one or more solid gripping configurations; and,
    a tubular collar, both the one or more gripping configurations and the tubular collar extending from an opposite side of the location portion to the upstand, the tubular collar including a free end of tubular collar defining a lowermost extremity of the device;
    wherein an internal dimension of the bore is dimensioned to closely receive the catheter to assist with maintaining a proper angle of insertion and decrease error.

2. The catheter placement device of claim 1, wherein the placement device is molded as a unitary device.

3. The catheter placement device of claim 1 wherein the device is at least partially translucent or transparent to assist the medical practitioner with a visual guide as to a location of a catheter within the device, during insertion.

4. The catheter placement device of claim 1 wherein the location portion includes a foot portion which, in use, is located to abut the patient's head through which the catheter is to be inserted.

5. The catheter placement device of claim 4 wherein the foot portion has a substantially planar lower surface.

6. The catheter placement device of claim 4 wherein the one or more gripping configurations extend from an underside of a preferred foot portion.

7. The catheter placement device of claim 6 wherein the gripping configuration includes at least two teeth extending from a lower surface of the location portion.

8. The catheter placement device of claim 4 wherein the tubular collar extends from the foot portion.

9. The catheter placement device of claim 1 wherein the tubular collar extends from a lower surface of the location portion to be located at least partially within a catheter entry opening formed in the patient's head.

10. The catheter placement device of claim 9 wherein the tubular collar is coaxial with the bore through the tubular upstand.

11. The catheter placement device of claim 9 wherein the tubular collar is annular in shape and is located centrally on the location portion.

12. The catheter placement device of claim 9 wherein an outer surface of the tubular collar tapers inwardly and downwardly.

13. The catheter placement device of claim 1 wherein the upstand is fixed relative to the location portion in order to maintain an angle of the bore relative to the location portion.

14. The catheter placement device of claim 1 wherein the upstand and the bore therethrough are substantially perpendicular to the location portion.

15. The catheter placement device of claim 1 wherein the upstand is approximately 25 mm in height.

16. The catheter placement device of claim 1, wherein the bore extends through the tubular collar.

* * * * *